United States Patent [19]

Lehman et al.

[11] Patent Number: 4,481,503

[45] Date of Patent: Nov. 6, 1984

[54] PRODUCTION MONITORING SYSTEM

[75] Inventors: F. Allen Lehman, Oklahoma City; William M. Sleffel, Moore; Malcolm G. Ray, Norman, all of Okla.

[73] Assignee: Kerr-McGee Corporation, Oklahoma City, Okla.

[21] Appl. No.: 403,281

[22] Filed: Jul. 29, 1982

[51] Int. Cl.³ .............................................. G01B 26/00
[52] U.S. Cl. ...................................... 340/518; 73/195; 340/606; 340/870.13
[58] Field of Search .................. 73/861, 195; 340/518, 340/529, 606, 870.03, 870.13, 870.09; 346/34

[56] References Cited

U.S. PATENT DOCUMENTS

| | | | |
|---|---|---|---|
| 3,103,644 | 9/1963 | Burton | 340/870.13 |
| 3,357,011 | 12/1967 | Diaz | 340/870.13 |
| 3,392,580 | 7/1968 | Bain et al. | 340/606 |
| 3,540,026 | 11/1970 | Scott | 340/606 |
| 4,246,576 | 1/1981 | Grieve et al. | 340/606 |
| 4,262,287 | 4/1981 | McLoughlin et al. | 340/606 |
| 4,340,886 | 7/1982 | Boldt | 340/518 |
| 4,353,118 | 10/1982 | Heimgartner et al. | 340/606 |

Primary Examiner—Herbert Goldstein
Attorney, Agent, or Firm—William G. Addison

[57] ABSTRACT

A production monitoring system wherein the velocity of fluid flowing through a monitored flowline is plotted with respect to time for a period of time sufficient to establish a repeatable pattern (production flow characteristics profile) and wherein an alarm value and an alarm delay time are determined from the production flow characteristics profile. In one aspect, the velocity of the fluid flowing through the monitored flowline is detected and an output indication indicating a problem production condition is provided in response to a detected velocity below the alarm value for a period of time in excess of the alarm delay time.

35 Claims, 9 Drawing Figures

FIG. 2

PRODUCTION MONITORING SYSTEM

BACKGROUND OF THE INVENTION

1. Field of the Invention

The present invention relates generally to systems for monitoring production in flowlines and, more particularly, but not by way of limitation, to a system for monitoring production in a flowline utilizing parameters established from a predetermined production flow characteristic profile.

2. Brief Description of the Prior Art

Off-shore oil fields generally have included a number of individual wells which were distributed over a considerable area of the sea floor into which the wells were drilled. In some such fields, it has been the practice to connect each well to a central collecting station by a flowline and the production from the various wells was collected at the central collecting station where the oil and gas was separated from the total fluids produced by the wells and, subsequently, such oil and gas were shipped or otherwise transported to shore-based facilities for further processing. In some instances, a tiered collection network was utilized where a number of sub-collecting stations were dispersed in the field with each sub-collecting station generally being located to collect production from a number of selected wells and the production collected at the various sub-collecting stations, then, was passed through a flowline to the central collecting station.

The production from individual wells fluctuated or varied with time and it has been difficult in the past to distinguish such fluctuations from problem conditions where something was interfering with production from the well, such as a malfunction in the equipment used to raise well fluids to the surface or a blocked or restricted flowline, for example. Detection of problem conditions in production from wells tended to increase in tiered collection networks, because the production from several wells, including the well associated with the problem production condition, was collected at the sub-collecting station and the total collected production was passed to the central collecting station. Thus, a problem production condition associated with a particular well might go undetected for a considerable length of time, since production would continue to flow from the sub-collecting station as a result of the production received from the other wells associated with the particular sub-collecting station.

In the past, personnel managing the field have engaged in extensive travel about the field to check conditions at the sub-collecting stations and at the well heads to determine if problem conditions in production existed. In many instances, it was necessary to open the various flowlines and conduct tests to determine if problem conditions in production existed in connection with the various individual wells.

SUMMARY OF THE INVENTION

The present invention provides a system for monitoring and detecting problem conditions in production from wells in off-shore fields in a more efficient, more economical and more positive manner which substantially reduces or eliminates the need for much of the previously required travel about the off-shore field and much of the testing of flow through the individual flowlines.

It has been discovered that fluctuations or variations in production (production flow characteristics profile) of individual wells or, more particularly, flowlines follow a pattern which is unique and often identifiable with respect to each such individual flowline and which, though varying from flowline to flowline, provides a means for identifying or detecting problem production conditions in individual flowlines. Once the production flow characteristics profile has been established for each individual flowline, the production flow from each of the flowlines is monitored and compared to parameters established from the production flow characteristics profile for the particular flowline to detect problem production conditions which might occur with respect to any particular individual flowline.

In the system of the present invention, production flow characteristic profiles are established for each monitored flowline by measuring the velocity of the flow of liquids in the monitored flowlines over a predetermined period of time. Utilizing the production flow characteristics profiles, a minimum value of the velocity of the liquids flowing in each monitored flowline is determined, a value below which a possible problem production condition might exist (such value being designated as the alarm value), and a minimum time period (designated as the alarm delay time) is established for each monitored flowline, the alarm delay time being the period of time which, if the flow velocity of liquids flowing in the monitored flowline is below the alarm value for a period of time greater than the alarm delay time, a problem production condition is determined to exist with respect to the production or fluid flow in that particular flowline.

In the monitoring system of the present invention, a transducer is externally connected to each monitored flowline, each transducer being adapted to measure the flow velocity of the fluid flowing in the monitored flowline and transmit a flow signal indicative of such measured flow velocity. The flow signals are received and processed and an audible or visually perceivable output indication is provided in the event that the flow velocity in any monitored flowline falls below the predetermined alarm value for a period of time in excess of the predetermined alarm delay time established for that particular monitored flowline.

DESCRIPTION OF THE PREFERRED EMBODIMENT

Figure 1:
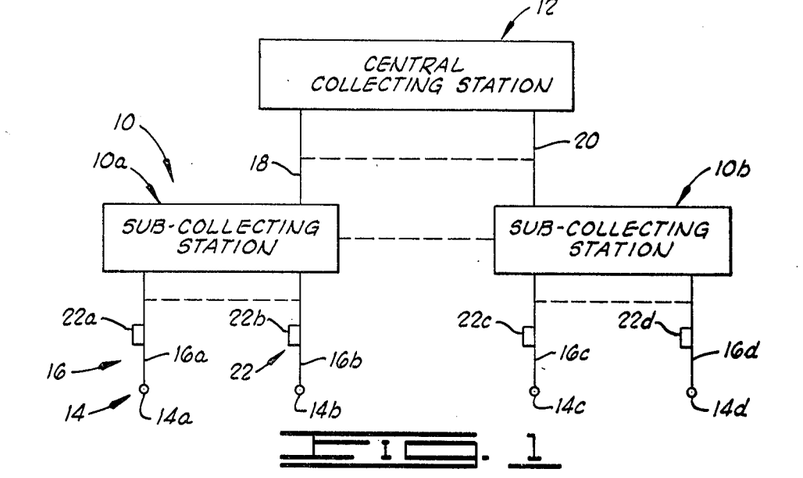
FIG. 1 is a schematic, diagrammatic drawing showing a producing off-shore field incorporating the system of the present invention.

Referring to FIG. 1, shown therein is a schematic drawing showing a portion of a producing off-shore oilfield having a plurality of sub-collecting stations 10 (only two sub-collecting stations being specifically shown in FIG. 1 and designated therein respectively by the reference numerals 10a and 10b). Centrally located among the sub-collecting stations 10 is a central collecting station 12.

Each of the sub-collecting stations 10, as shown in FIG. 1, is associated with a plurality of producing wells 14 drilled to an oil and gas bearing formation and each well either is free-flowing or includes an artificial lifting system (not shown) delivering fluid to a flowline extending from the well 14 to one of the associated sub-collecting stations 10. For example, the sub-collecting station 10a is associated with a plurality of wells 14 (only two wells 14 being specifically shown in FIG. 1 and designated therein by the respective reference numerals 14a and 14b) and the sub-collecting station 10b is associated with a plurality of wells 14 (only two wells 14 being specifically shown in FIG. 1 and designated therein by the respective reference numerals 14c and 14d). A flowline 16 is connected to each of the wells 14 and each flowline 16 extends from one of the wells 14 to one of the sub-collecting stations 10. For example, the flowline extending from the well 14a to the sub-collecting station 10a is designated in FIG. 1 by the reference numeral 16a, the flowline extending from the well 14b to the sub-collecting station 10a is designated in FIG. 1 by the reference numeral 16b, the flowline extending from the well 14c to the sub-collecting station 10b is designated in FIG. 1 by the reference numeral 16c and the flowline extending from the well 14d to the sub-collecting station 10b is designated in FIG. 1 by the reference numeral 16d.

The fluid flow (production) from each of the wells 14 passes through one of the respective flowlines 16 to one of the sub-collecting stations 10. At each of the sub-collecting stations 10, the fluid flow received from the wells 14 through the respective flowlines 16 is combined and the total, combined fluid flow is passed from the sub-collecting station 10 to the central collecting station 12 by way of a flowline which is connected to and extends between the respective sub-collecting station 10 and the central collecting station 12 (the flowline extending between the sub-collecting station 10a and the central collecting station 12 being designated in FIG. 1 by the reference numeral 18 and the flowline extending between the sub-collecting station 10b and the central collecting station 12 being designated in FIG. 1 by the reference numeral 20).

The central collecting station 12 receives the fluid flow from the sub-collecting stations 10 from the flowlines 18 and 20. The central collecting station 12 may include a treating station (not shown) for separating the oil and gas from the fluid flow received from the various wells, in a manner well known in the art. Subsequently, the oil and gas is transported from the central collecting station 12 to land based facilities for further treatment.

It should be noted that, in some applications, the flowlines 18 and 20 each are disposed on the sea floor and each includes a portion which extends generally upwardly from the sea floor toward one of the sub-collecting stations 10 and another portion which extends upwardly from the sea floor toward the central collecting station 12. In some other applications, one or more of the flowlines 18 or 20 may be disposed above the water where the particular sub-collecting station 10 is relatively near the central collecting station 12. Each of the flowlines 16 is disposed on the sea floor and each extends from one of the wells 14 to one of the sub-collecting stations 10, each including a portion which extends generally upwardly from the sea floor toward one of the sub-collecting stations 10.

Figure 2:
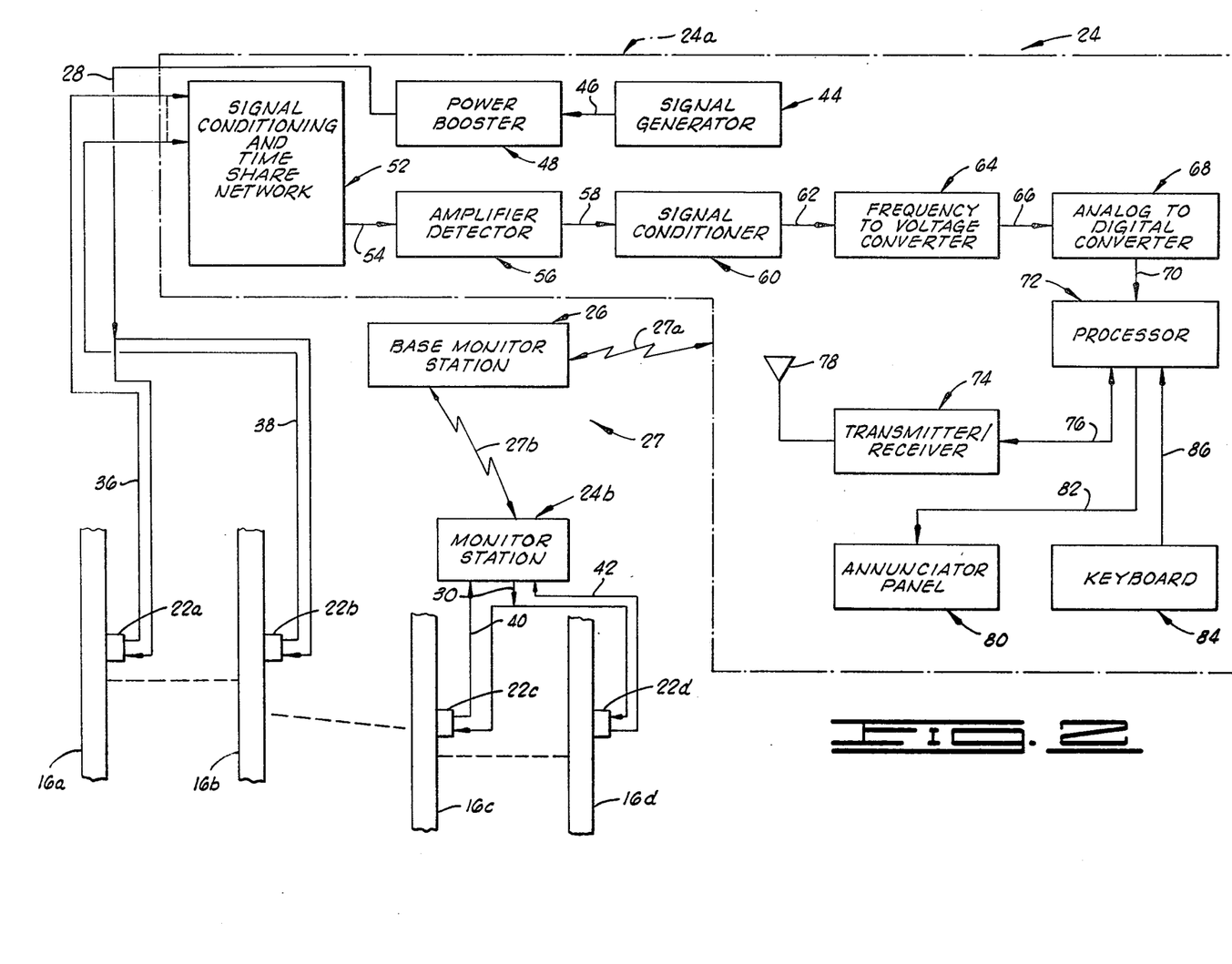
FIG. 2 is a schematic, diagrammatic view of a portion of the monitoring system of the present invention.
Figure 3:
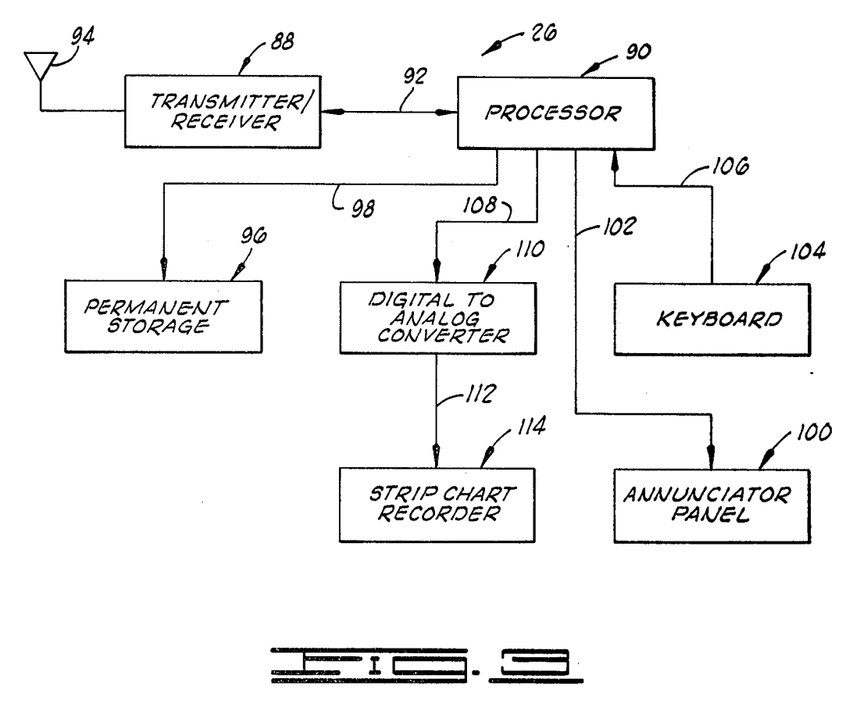
FIG. 3 is a schematic view of another portion of the monitoring system of the present invention.

In the system of the present invention, the flow of fluid through each of the flowlines 16 (the monitored flowlines) is monitored by means of a monitoring system which is shown schematically in FIGS. 2 and 3. The monitoring system generally comprises a plurality of transducers 22, one of the transducers 22 being connected externally to each of the flowlines 16 to be monitored, a plurality of monitor stations 24, each monitor station 24 being located on one of the sub-collecting stations 10 (two monitor stations being shown in FIG. 2 and designated therein by the reference numerals 24a and 24b, respectively), and a base monitor station 26 which is located on the central collecting station 20 (the base monitor station 26 being shown in detail in FIG. 3). The monitor stations 24a and 24b are identical in construction and, thus, only the monitor station 24a is shown in detail in FIG. 2.

Each of the monitor stations 24 is in communication with the base monitor station 26 by way of a radio communication link 27 (the radio communication link between the monitor station 24a and the base monitor station 26 being shown in FIG. 2 and designated therein by the reference numeral 27a, and the radio communication link between the monitor station 24b and the base monitor station 26 being shown in FIG. 2 and designated therein by the reference numeral 27b). As indicated in FIG. 2, the radio communication link 27 between the monitor stations 24 and the base monitor station 26 is a two-way radio communication link, for reasons to be described in greater detail below.

Each of the transducers 22 is externally mounted on or otherwise connected to one of the flowlines 16 to be monitored, the transducers on the flowlines 16a, 16b, 16c and 16d being diagrammatically shown in FIGS. 1 and 2 and individually designated therein by the respective reference numerals 22a, 22b, 22c and 22d. Each of the transducers 22 is constructed and adapted to sense or measure the flow of fluid through one of the monitored respective flowlines 16. Each transducer 22 provides an output flow signal indicative of or, more particularly, proportional to the velocity (flow velocity) of the fluid flowing through one of the monitored flowlines 16.

While the transducers 22 may be of any appropriate construction, it has been determined that ultrasonic Doppler shift transducers of the type manufactured by Bestobell Meterflow Ltd. of Baldock, Herts, England and designated by the Bestobell model designation DS-5, T-30 or P10, for example, provide satisfactory results when used in the system of the present invention. It should be noted that the Bestobell transducers just identified by model designations are complete flow meter systems including transducers and the associated Doppler electronics and, in the monitoring system of the present invention, it is necessary to utilize only the transducer portion of such systems. Similar transducers are commercially available from other sources.

A transducer of the type just described is constructed to receive a signal having a frequency in the ultrasonic frequency range, such as 625 KHz or 640 KHz depending on the particular transducer, for example. In general, the transducer transmits the ultrasonic frequency signal into the flowline and the signal transmitted or beamed into the flowline is reflected off particles in the fluid or gas bubbles flowing through the flowline. The reflected signal is transmitted by the transducer as the transducer output flow signal. The reflected signal transmitted by the transducer has a carrier frequency in 625 KHz or 640 KHz range, for example, and is modulated in proportion to the velocity of the fluid flowing through the flowline. Thus, the transducer senses or measures the velocity of the fluid flowing through the flowline and the transducer provides an output signal which is directly proportional to the velocity of the fluid flowing through the flowline.

A transducer of the type just described is constructed to be mounted on a flowline and this type of transducer does not include any component or element which must intrude into the flowline or, in other words, this is a non-intrusive type of transducer. Utilizing this type of transducer eliminates the necessity of having to modify the flowline by cutting or welding or the like and, thus, provides a transducer which can be installed on existing flowlines in a faster, more economical manner.

Also, it should be noted that transducers of the type just described typically are adapted to measure flow velocity with relatively great accuracy, provided the percent of suspended particles in the fluid is low, and the flowline substantially is full of flowing fluid. The present system utilizes trends in the fluid flow and the accuracy of the measured velocity of the fluid flow is not critical. Thus, the conditions under which such transducers accurately measure the velocity of the fluid flow are not critical factors in the utilization of such transducers in the present system.

As shown in FIG. 2, each of the transducers 22a and 22b, receives an ultrasonic frequency transducer operating signal on a signal path 28 and each of the transducers 22c and 22d receives an ultrasonic frequency transducer operating signal on a signal path 30. Each of the transducers 22a, 22b, 22c and 22d is adapted to provide an output flow signal on a signal path 36, 38, 40 and 42, respectively. The output flow signal provided by each of the transducers 22a, 22b, 22c and 22d is proportional to the velocity of the fluid flowing through one of the monitored flowlines 16a, 16b, 16c and 16d, respectively.

The transducer operating signals on the signal paths 28 and 30 are provided by the monitor stations 24, as shown in FIG. 2, the monitor station 24a providing the transducer operating signal on the signal path 28 and the monitor station 24b providing the transducer operating signal on the signal path 30. As mentioned before, the monitor stations 24 are identical in construction and operation. Thus, only the monitor station 24a is shown in detail in FIG. 2 and the description herein relating to the monitor station 24a applies equally to the other monitor stations 24 in the system of the present invention.

Each of the monitor stations 24 includes a signal generator 44 which is constructed and adapted to provide an output signal having a frequency in the ultrasonic frequency range, such as 625 KHz or 640 KHz, for example, depending on the construction of the particular transducer being utilized in a particular monitoring system. The signal generator 44 output signal is provided on a signal path 46 which is connected to the input of a power booster 48. The power booster 48 is constructed and adapted to receive the signal generator 44 output signal and to increase the power level of the received signal generator 44 output signal, the power booster 48 providing an output signal on a signal path 50.

The power booster 48 is a unity gain buffer amplifier. In the past, the length of the cable connecting the transducers 22 to the signal generator 44 or, in other words, the source of the transducer operating signal has been limited to a relatively short length, the particular length being somewhat dependent upon the type of cable being utilized in a particular application. In the past, if this cable length exceeded a predetermined maximum length which was relatively short, signal distortion occurred. It has been found that, by utilizing the power booster 48 to increase the power level of the signal without increasing the gain, the length of the cable (the signal paths 28 and 30) could be increased without encountering signal distortion. This feature particularly is significant in the present system where the transducers 22 may be located a relatively large distance from the signal generator 44.

The flow signals provided by the transducers 22a and 22b are connected to and received by a time share network 52 (referred to in FIG. 2 as "signal conditioning and time share network"). Referring particularly to the transducers 22a and 22b, the output flow signals provided by the transducers 22a and 22b on the signal paths 36 and 38, respectively, are connected to and received by the time share network 52, as shown in FIG. 2. In one preferred embodiment, the time share network 52 initially amplifies each of the received flow signals so that each of the received flow signals substantially is at the same power level. After the received flow signals have been amplified, the time share network 52 then multiplexes the input flow signals received from the transducers 22a and 22b and sequentially provides the input flow signals on a time share network 52 output signal path 54. In one particular application, the time share network 52 was adapted to receive a flow signal from each transducer at least one time per second during the operation of that particular system. Time share networks which are constructed to multiplex input signals and sequentially provide the input signals on an output signal path are commercially available and well known in the art, and thus a detailed description of the construction and operation of the time share network 52 is not deemed necessary.

The flow signals sequentially provided on the output signal path 54 from the time share network 52 are connected to and received by an amplifier detector 56. The amplifier detector 56 is constructed to detect or demodulate the received flow signals and to amplify the demodulated flow signals, the demodulated flow signals being provided on an amplifier detector output signal path 58.

The demodulated flow signals provided on the amplifier detector 56 output signal path 58 are connected to and received by a signal conditioner 60. The signal conditioner 60 includes an amplifier for amplifying the received signals, a low pass filter which is adapted to pass all frequencies below a specified or predetermined frequency with relatively little or no loss while discriminating against higher frequencies, and a Schmitt trigger for reducing noise. The output signals from the signal conditioner 60 are provided on a signal path 62. Each of the signals provided on the signal path 62 has a frequency which is directly proportional to the velocity of the flow of fluid through one of the monitored flowlines.

The output signals from the signal conditioner 60 provided on the signal path 62 are connected to and received by a frequency to voltage converter 64. The frequency to voltage converter 64 provides an output signal on a signal path 66 which is a direct current signal having a voltage which is proportional to the frequency of the signal received by the frequency to voltage converter 64. Thus, the voltage of each of the signals provided on the signal path 66 is directly proportional to the velocity of the fluid flowing through one of the monitored flowlines. In one particular operating system, the DC voltage of each of the signals provided on the signal path 66 was between zero and ten (10) volts depending on the velocity of the fluid flow, for example.

The frequency to voltage converter 64 output signal on the signal path 66 is connected to and received by an analog to digital converter 68. The analog to digital converter 68 is constructed to convert the voltage of the received input signal to a digital or binary form and to provide the binary signal on an output signal path 70. The analog to digital converter 68 output signal on the signal path 70 is connected to and received by a processor 72. Thus, the flow signals received from the transducers 16a and 16b by the monitor station 24a are sequentially connected to and received by the processor 72. More particularly, the processor 68 receives the analog to digital converter 70 output signals, each of which is indicative of the velocity of the fluid flowing through one of the monitored flowlines and, thus, the signals on the signal path 70 sometimes are referred to herein simply as the flow signals.

The processor 72 is connected to a transmitter-receiver 74 by way of a signal path 76. The transmitter-receiver 74 is constructed to receive signals from the processor 72 on the signal path 76 and to transmit the received signals by way of an antenna 78 over the radio communication link 27a. Also, the transmitter-receiver 74 is constructed to receive transmitted signals by way of the antenna 78 over the radio communication link 27a, such received signals being connected to and received by the processor 72 on the signal path 76.

An annunciator panel 80 is connected to the processor 72 by way of a signal path 82. The annunciator panel 80 is constructed to provide a visually perceivable output indication in response to receiving an alarm signal from the processor 72 on the signal path 82. In one model, the annunicator panel 80 consisted of a plurality of lights, each light being associated with one of the monitored flowlines, and, in this application, the annunicator panel 80 was constructed to illuminate one of the lights in response to receiving an alarm signal from the processor 72 indicating that a problem production condition existed with respect to one particular monitored flowline.

Each monitor station 24 also includes a keyboard 84 which is connected to the processor 72 by way of a signal path 86. The keyboard 84 is constructed to provide a means for manually inputting data into the processor 72 during the operation of the system of the present invention. In a preferred embodiment, an alpha-numeric display is interfaced with the keyboard 84 to provide a visually perceivable display of the data being inputted into the processor 72 by way of the keyboard 84.

As shown in FIG. 3, the base monitor station 26 includes a transmitter-receiver 88 which is connected to a processor 90 by way of a signal path 92. The transmitter-receiver 88 is constructed to receive data transmitted on a predetermined radio frequency over the radio communication links 27 by way of an antenna 94 and to provide such received data to the processor 90 on the signal path 92. The transmitter-receiver 88 also is constructed to receive data from the processor 90 on the signal path 92 and to transmit such received information by way of the antenna 94 over the radio communication link 27.

As shown in FIG. 3, the base monitor station 26 also includes a permanent storage 96 which is connected to the processor 90 by way of a signal path 98. The permanent storage 96 is constructed to receive data from the processor 90 on the signal path 98 and to store such received data. In a particular embodiment, the permanent storage 96 may be adapted to store the received data on any desired permanent storage medium such as a magnetic tape or disc type storage medium, for example. The processor 90 is programmed to provide data to the permanent storage 96 in response to receiving a store data command manually inputted into the processor 90 by a keyboard to be discussed below.

An annunciator panel 100 is connected to the processor 90 by way of a signal path 102. The annunciator panel 100 is constructed to provide a visually perceivable output indication in response to receiving an alarm signal from the processor 90 on the signal path 102. In one model, the annunicator panel 100 consisted of a plurality of lights, each light being associated with one of the monitored flowlines, and, in this application, the annunicator panel 100 was constructed to illuminate one of the lights in response to receiving an alarm signal from the processor 90 indicating that a problem production condition existed with respect to one of the monitored flowlines.

The base monitor station 26 also includes a keyboard 104 which is connected to the processor 90 by way of a signal path 106. The keyboard 104 is constructed to provide a means for manually inputting data into the processor 90 during the operation of the system of the present invention. In a preferred embodiment, the keyboard 104 is interfaced with an alpha-numeric display to provide a visually perceivable display of the data being inputted into the processor 90 by way of the keyboard 104.

The processor 90 has an output signal path 108 which is connected to a digital to analog converter 110. The digital to analog converter 110 is constructed and adapted to receive data from the processor 90 on the signal path 106 in a digital form and to convert such received data from the digital form to an analog form of signal, the converted analog form of the received data being provided by the digital to analog converter 110 on a signal path 112. The signal path 112 is connected to a strip chart recorder 114 and the strip chart recorder 114 is constructed and adapted to receive the data in an analog form of signal from the digital to analog converter 110 and to provide a printed chart output displaying the received data in a chart or plot form. The processor 90 is programmed to provide the data to the strip chart recorder 114 in response to receiving a print command signal which is manually inputted into the processor 90 by the keyboard 104.

The velocity of the fluid flowing through a monitored flowline of the type contemplated by the system of the present invention varies with time, and variations or fluctuations in the velocity with time vary from one monitored flowline to another monitored flowline. The production flow characteristics profile of a particular monitored flowline produces an identifiable pattern which is unique to the particular monitored flowline, and the alarm value and the alarm delay time are determined for each monitored flowline, such as the flowlines 16a, 16b, 16c and 16d, for example. In practicing the system of the present invention, initially, it is necessary to plot or, otherwise, determine the velocity of the fluid flowing through each monitored flowline with respect to time over a period of time sufficient to establish a repeatable pattern, this plot or determination being referred to herein as the production flow characteristics profile.

In a particular production flow characteristics profile generally there will be peak or maximum velocities which occur at various time intervals. The alarm value for a particular monitored flowline is selected to be a velocity below such peak or maximum velocity values determined from the production flow characteristics profile for that particular monitored flowline and, more particularly, the alarm value for each monitored flowline preferrably is selected to be a velocity in the range of about fifty percent to about twenty percent of the peak or maximum velocity values determined from the respective production flow characteristics profiles for the monitored flowlines.

The production flow characteristics profile also is utilized to determine the alarm delay time. As a minimum, the alarm delay time should be selected to be a period of time in excess of a predetermined minimum period of time, so problem production conditions are not indicated in response to one-time or momentary changes in the velocity of the fluid flowing through one of the monitored flowlines. With respect to particular production flow characteristics profiles, the alarm delay time should be selected to be a period of time sufficient to encompass at least about three major or peak velocity values determined from the respective production flow characteristics profiles or the predetermined minimum period of time, whichever is greater.

In some instances, particular production flow characteristics profiles may not include any major or peak velocity values or, in other words, the velocity of the fluid flowing through such monitored flowline is relatively constant. In these instances, the alarm value should be set at a value generally along and generally slightly below the lower limit of the velocity values and the alarm delay time should be set at the predetermined minimum period of time.

In one embodiment of the present invention, the minimum period of time or minimum alarm delay time was selected to be ten minutes. In this embodiment, the alarm delay time was selected in five minute increments from the minimum alarm delay time of ten minutes, so the determined alarm delay time encompassed at least about three major or peak velocity values determined from the respective production flow characteristics profiles or the minimum alarm delay time of ten minutes, whichever was greater.

Figure 4:
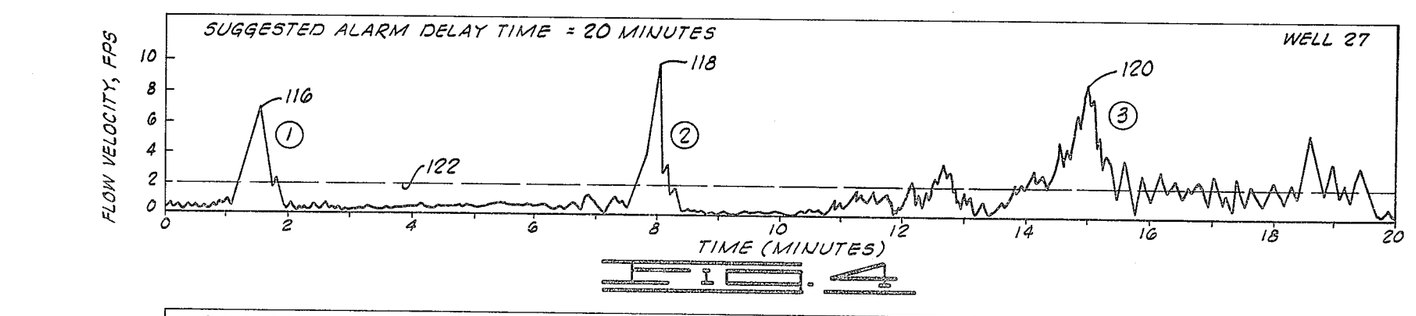
FIG. 4 is a graphic representation of the production flow characteristics profile of a particular flowline for illustrating certain aspects of the present invention.

Shown in FIG. 4 is a portion of a production flow characteristics profile of one monitored flowline for the purpose of illustrating certain aspects of the present invention. More particularly, the velocity of the fluid flowing through a monitored flowline is plotted in FIG. 4 versus time during a period of time when the fluid is flowing through such monitored flowline in a normal, unobstructed manner. In particular, FIG. 4 is a graphical representation of the flow velocity through a monitored flowline observed over a period of time equal to twenty minutes, such flow velocity in terms of feet per second being plotted on the ordinate and the time, in minutes, being plotted on the abscissa. As shown in FIG. 4, production (fluid flow) through a monitored flowline, having such a production flow characteristics profile, occurs at intervals with little or no flow occurring between such production (fluid flow) intervals. In this instance, referring to the production flow characteristics profile shown in FIG. 4, the first three major peaks (designated in FIG. 4 by the reference numerals 116, 118 and 120 and the symbols of the encircled numerals 1, 2 and 3) occurred within a period of time of about fifteen minutes. Thus, the alarm delay time was selected to be twenty minutes, a period of time sufficient to encompass the three major peaks 116, 118 and 120 and selected in five minute increments above the minimum alarm delay time of ten minutes. The peak or maximum velocity (peak 118) noted with respect to this particular production flow characteristics profile shown in FIG. 4 was about ten feet per second and, thus, the alarm value was selected to be two feet per second, as indicated by the dashed-line 122 in FIG. 4, a value equal to twenty percent of the peak or maximum velocity value.

Figure 5:
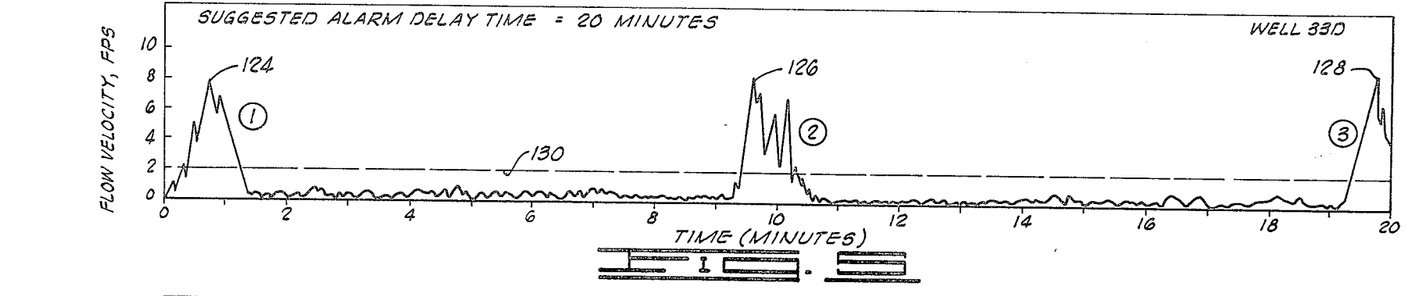
FIG. 5 is a graphic representation, similar to FIG. 4, but showing the production flow characteristics profile of another particular flowline.

Shown in FIG. 5 is a portion of another production flow characteristics profile for another monitored flowline, the flow velocity in terms of feet per second being plotted on the ordinate and the time in minutes being plotted on the abscissa. In this instance referring to the production flow characteristics profile shown in FIG. 5, the first three major peaks (designated in FIG. 5 by the reference numerals 124, 126 and 128 and the symbols of encircled numerals 1, 2 and 3) occurred within a period of time slightly less than twenty minutes. In this instance, the alarm delay time was selected to be twenty minutes, a period of time sufficient to encompass the three major peaks 124, 126 and 128 and selected in five minute increments above the minimum alarm delay time of ten minutes. The peak or maximum velocity (peak 128) noted with respect to this particular production flow characteristics profile shown in FIG. 5 was about nine feet per second and, thus, the alarm value was selected to be two feet per second as indicated by the dashed-line 130 in FIG. 5, a value slightly greater than twenty-two percent of the peak or maximum velocity value.

Figure 6:
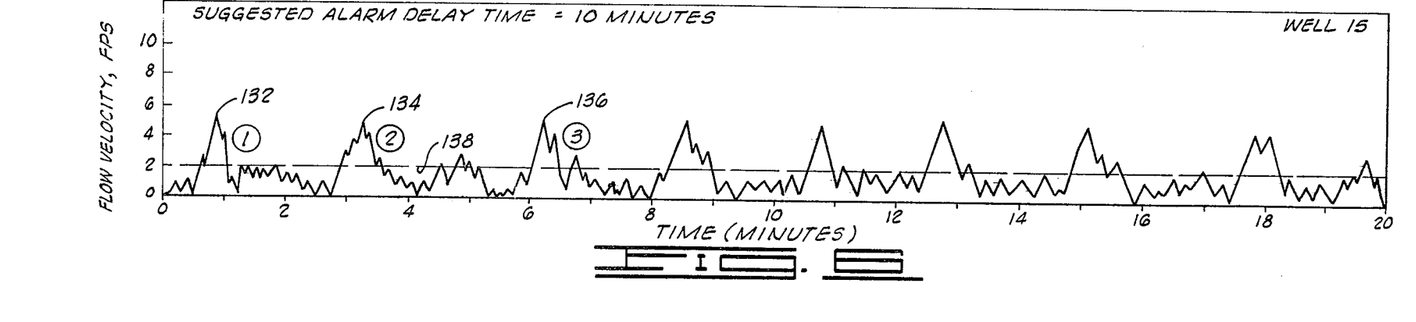
FIG. 6 is a graphic representation, similar to FIGS. 4 and 5, but showing the production flow characteristics profile of yet another particular flowline.

Shown in FIG. 6 is a portion of still another production flow characteristics profile for another flowline, the flow velocity in terms of feet per second being plotted on the ordinate and the time in minutes being plotted on the abscissa. In this instance referring to the production flow characteristics profile shown in FIG. 6, the first three major peaks (designated in FIG. 6 by the reference numerals 132, 134 and 136 and the symbols of encircled numerals 1, 2 and 3) occurred within a period of time of about five and one-half minutes. Since the increment of time (five and one-half minutes) during which the first three major peaks occurred was less than the minimum alarm delay time of ten minutes, the alarm delay time was selected to be ten minutes in this instance referring to the production flow characteristics profile shown in FIG. 6. The peak or maximum velocity (peak 132) noted with respect to this particular production flow characteristics profile shown in FIG. 6 was about five and one-half feet per second and, thus, the alarm value was selected to be two feet per second, as indicated by the dashed-line 138 in FIG. 6, a value slightly greater than thrity-six percent of the peak or maximum velocity value.

Figure 7:
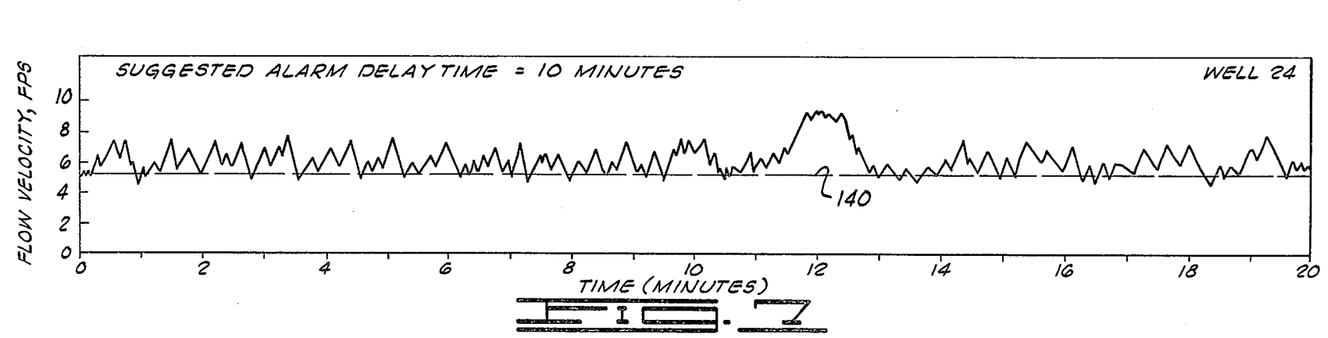
FIG. 7 is a graphic representation, similar to FIGS. 4, 5 and 6, but showing the production flow characteristics profile of still another particular flowline.

Shown in FIG. 7 is still another production flow characteristics profile for another monitored flowline, the flow velocity in terms of feet per second being plotted on the ordinate and the time in minutes being plotted on the abscissa. With respect to this particular production flow characteristics profile shown in FIG. 7, there were no major peaks or, in other words, the flow velocity through this particular monitored flowline was relatively constant. Thus, the alarm delay time was selected to be ten minutes, a value equal to the minimum alarm delay time. Since the velocity of the fluid flowing through this particular monitored flowline was relatively constant, the alarm value was selected to be a value generally at and generally below the minimum flow velocities, the alarm value being selected at about five feet per second as indicated by the dashed-line 140 in FIG. 7.

Figure 8:
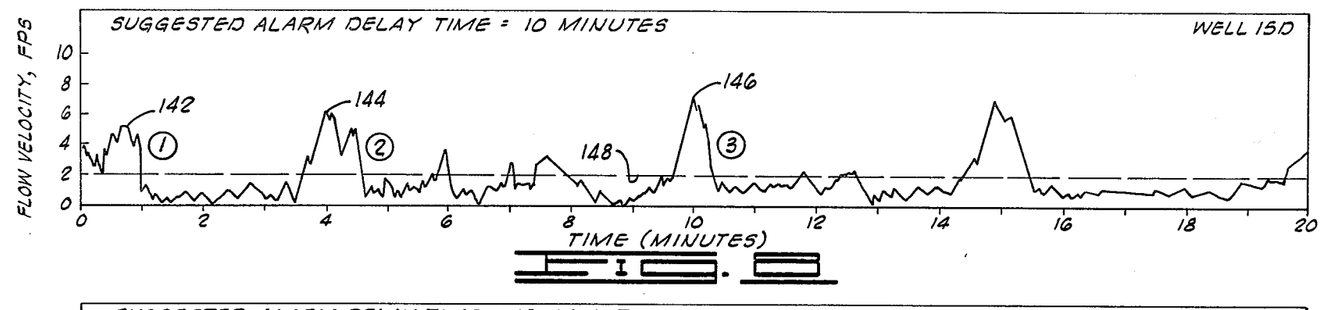
FIG. 8 is a graphic representation, similar to FIGS. 4, 5, 6 and 7, but showing the production flow characteristics profile of another particular flowline.

Shown in FIG. 8 is another production flow characteristics profile of another monitored flowline, the flow velocity in feet per second being plotted on the ordinate and the time in minutes being plotted on the abscissa. In this instance referring to the production flow characteristics profile shown in FIG. 8, the first three major peaks (designated in FIG. 8 by the reference numerals 142, 144 and 146 and the symbols of encircled numerals 1, 2 and 3) occurred within a period of time of slightly less than ten minutes. Thus, the alarm delay time was selected to be ten minutes, the minimum alarm delay time. The peak or maximum velocity (peak 146) noted with respect to this particular production flow characteristics profile shown in FIG. 8 was about seven and one-half feet per second and, thus, the alarm value was selected to be two feet per second, as indicated by the dashed-line 148 in FIG. 8, a value somewhat greater than twenty-six percent of the peak or maximum velocity value.

Figure 9:
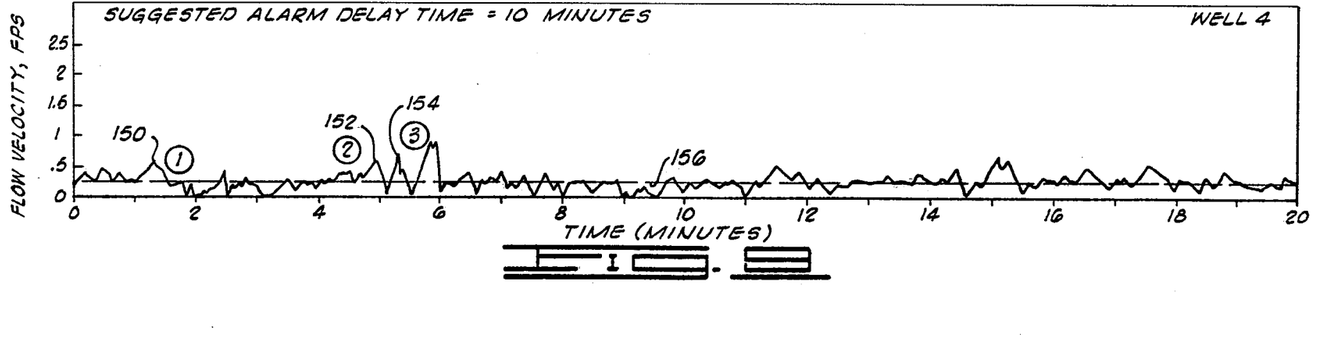
FIG. 9 is a graphic representation, similar to FIGS. 4, 5, 6, 7 and 8, but showing the production flow characteristics profile of yet another flowline.

Shown in FIG. 9 is yet another production flow characteristics profile of another monitored flowline, the flow velocity in terms of feet per second being plotted on the ordinate and the time in minutes being plotted on the abscissa. In this instance referring to the production flow characteristics profile shown in FIG. 9, the first three major peaks (designated in FIG. 9 by the reference numerals 150, 152 and 154 and the symbols of the encircled numerals 1, 2 and 3) occurred within a period of time of slightly greater than five minutes. Thus, the alarm delay time was selected to be ten minutes, the value of the minimum alarm delay time. The peak or maximum velocity (peak 154) noted with respect to this particular production flow characteristics profile shown in FIG. 9 was about eight tenths foot per second and, thus, the alarm value was selected to be twenty-five one hundredths foot per second, as indicated by the dashed-line 156 in FIG. 9, a value slightly greater than thirty-one percent of the peak or maximum velocity value.

During one phase (a calibration phase) of the operation of the monitoring system of the present invention, the signal generator 44 generates and provides transducer operating signals on the signal path 46, the transducer operating signals being provided on the signal path 28 through the power booster 48. The transducer operating signals on the signal path 28 are provided to the transducers 22. As shown in FIG. 2 and with respect to the flowlines 16a and 16b, the transducer operating signal on the signal path 28 is connected to the transducers 22a and 22b, respectively.

The transducers 16 provide the flow signals with each transducer 22 providing a flow signal proportional to the flow velocity of the fluid flowing through the flowline associated with or connected to that particular transducer 22. Referring to FIG. 2 and with respect to the particular transducers 22a and 22b, each transducer 22a and 22b provides an output flow signal on the respective signal path 36 and 38 which is proportional to the velocity of the fluid flowing through the flowline 16a and 16b, respectively. The flow signals provided on the signal paths 36 and 38 are connected to and received by the time share network 52.

After amplifying the received flow signals, the time share network 52 functions to sequentially provide the flow signals received from the transducers 22a and 22b on the output signal path 54. The received flow signals on the signal path 54 are amplified and detected by the amplifier detector 56, conditioned through the signal conditioner 60, and, then, passed through the frequency to voltage converter 64. The frequency to voltage converter 64 functions to convert each of the received flow signals to a DC voltage analog of the flow signals received on the input signal path 64 and each of the flow signals in a DC voltage analog form are sequentially provided on the frequency to voltage converter 64 output signal path 66. The flow signals in an analog form on the signal path 66 are received by the analog to digital converter 68 and the analog to digital converter 68 provides the flow signals in a binary form on the signal path 70.

The processor 72 receives sequentially each of the flow signals provided on the signal path 70. During this calibration phase, the processor 72 is programmed to provide the received flow signals on the output signal path 76, such flow signals being provided to the transmitter-receiver 74. The transmitter portion of the transmitter-receiver 74 transmits the received flow signals on a radio frequency carrier over the radio communication link 27a, such flow signals being transmitted by way of the antenna 78.

The flow signals transmitted by the transmitter-receiver 74 in the monitor station 24a are received by way of the antenna 94 in the base monitor station 26. The flow signals received at the base monitor station 26 during the calibration phase are received by the receiver portion of the transmitter-receiver 88 and the received flow signals are provided on the transmitter-receiver 88 output signal path 92. The processor 90 in the base monitor station 26 is programmed to receive the flow signals on the signal path 92 and to store the received flow signals during this calibration phase of the operation, along with the relative time each such flow signal was received.

During the calibration phase, the flow signals are produced at each of the monitor stations 24 and each monitor station 24 transmits the flow signals to the base monitor station 26 in a manner exactly like that described before with respect to the monitor station 24a. Thus, the base monitor station 26 receives the flow signals from each of the monitor stations 24 and the processor 90 in the base monitor station 26 is programmed to receive and store the flow signals and the relative times during this calibration phase. Further, the processor 90 is programmed to store each of the received flow signals along with a code identifying the particular monitored flowline 16 associated with each such flow signal and the time at which each such flow signal was received at the processor 90. Since the flow signals are sequentially produced as a result of multiplexing the transducers 22 at each of the monitor stations 24, the particular flowline 16 associated with each flow signal is determined by the processors 72 and 90 as a result of the order in which such flow signals are received along with identifying the particular monitor station 24 from which such flow signals are received.

After the flow signals have been stored in the processor 90 for a predetermined period of time sufficient to establish the production flow characteristics profiles for the monitored flowlines 16, the processor 90 is programmed to provide the stored flow signals received from each of the transducers 22 and the relative time each such flow signal was received on the output signal path 108 in response to a received print command signal manually inputted into the processor 90 by way of the keyboard 104. More particularly, the print command signal is manually inputted into the processor 90 along with a code identifying a particular monitored flowline 16 and, in response, the processor 90 provides the stored flow signals and the relative times related to that particular flowline 16 on the output signal path 108. The flow signals and the relative times on the signal path 108 provided by the processor 90 are in a digital form and the digital to analog converter 110 converts the received flow signals to an analog form of signal, the flow signals in an analog form being provided on the signal path 112. The flow signals and the relative times in an analog form on the signal path 112 are received by the strip chart recorder 114 and the strip chart recorder 114 is adapted to provide an output in a printed form of a plot of the received flow signals with respect to time, such plot being the production flow characteristics profile. The production flow characteristics profile is produced by the strip chart recorder 114 for each of the monitored flowlines 16 in the manner just described, during the calibration phase.

Utilizing the production flow characteristics profiles produced by the strip chart recorder 114, the alarm value and the alarm delay time are determined for each of the monitored flowlines 16 in a manner like that described before with respect to FIGS. 4, 5, 6, 7, 8 and 9. The established alarm values and alarm delay times for each of the monitored flowlines 16 are manually inputted into the processor 90 by way of the keyboard 104. The processor 90 is programmed to receive and store the alarm value and the alarm delay time for each of the monitored flowlines 16. Also, the processor 90 is programmed to provide the alarm value and the alarm delay time for each of the monitored flowlines 16 on the output signal path 92, the alarm values and the alarm delay times being received by the transmitter-receiver 88. The transmitter portion of the transmitter-receiver 88 transmits the received alarm values and alarm delay times by way of the antenna 94.

The alarm values and the alarm delay times transmitted by the transmitter-receiver 88 of the base monitor station 26 are received by the monitor stations 24, or referring particularly to the monitor station 24a, the alarm values and the alarm delay times are received by the antenna 78 of the monitor station 24a. The alarm values and alarm delay times are received by the receiver portion of the transmitter-receiver 74 and the received alarm values and alarm delay times are provided on the transmitter-receiver 74 output signal path 76 for reception by the processor 72. The processor 72 of the monitor station 24a is programmed to receive the alarm values and alarm delay times from the transmitter-receiver 74 and to store the received alarm values and alarm delay times. In a similar manner, the alarm values and the alarm delay times are received and stored at the other monitor stations 24.

During one other phase (the monitoring phase) of the operation of the monitoring system of the present invention, the signal generator 44 provides the transducer operating signals to the transducers 22 in a manner exactly like that described before with respect to the providing of the transducer operating signals during the calibration phase. Each of the transducers 22 provides an output flow signal which is proportional to the velocity of the fluid flowing through the monitored flowline associated with or connected to the particular transducer 22, such as the flow signals provided by the transducers 22a and 22b on the signal paths 36 and 38. The flow signals from the transducers 22a and 22b are received by the time share network 52 and, after amplifying the received flow signals, the time share network 52 sequentially provides the received flow signals on the output signal path 54. The flow signals provided on the signal path 54 are amplified and detected by the amplifier detector 56, conditioned through the signal conditioner 60, converted to an analog DC voltage by the frequency to voltage converter 64, and converted to a digital form of signal by the analog to digital converter 68. The flow signals in a digital form are provided on the signal path 70.

During the monitoring phase, the processor 72 is programmed to receive the flow signals provided on the signal path 70 and to compare each of the received flow signals with the alarm value established for the monitored flowline 16 associated with such received flow signal, such as the monitored flowlines 16a and 16b shown in FIG. 2, for example. In the event any of the compared flow signals is smaller than the predetermined alarm value established for the monitored flowline 16 associated with that flow signal for the predetermined alarm delay time established for the monitored flowline 16 associated with that flow signal, the processor 72 is programmed to provide an output no flow signal on the signal path 82.

The annunciator panel 80 receives the signals on the output signal path 82 from the processor 72 and the annunciator panel 80 is constructed to provide a visually perceivable output indication in response to receiving a no flow signal on the signal path 82. The annunciator panel 80 includes a plurality of indicators (not shown in the drawings) with each such indicator being associated with one of the monitored flowlines 16. The annunciator panel 80 is constructed to provide a visually perceivable output indication in response to receiving a no flow signal on the signal path 82 from the processor 72 indicating a problem production condition in the monitored flowline producing the flow signal which resulted in the no flow signal being produced by the processor 72. In one form, for example, the annunciator panel 80 could include a plurality of lamp indicators with each lamp indicator being positioned on the annunciator panel 80 such that each lamp indicator would be associated with one of the monitored flowlines 16.

During the monitoring phase, the processor 72 also is programmed to provide the flow signals received on the signal path 70 on the output signal path 76 for reception by the transmitter-receiver 74. The transmitter-receiver 74 transmitts the received flow signals by way of the antenna 78.

During the monitoring phase, the flow signals transmitted by the monitor station 24a are received by the antenna 94 at the base monitor station 26. The flow signals received from the monitor stations 24a are received by the receiver portion of the transmitter-receiver 88 and the transmitter-receiver 88 is adapted to provide the received flow signals on the output signal path 92.

The flow signals provided on the output signal path 92 are received by the processor 90. During the monitoring phase, the processor 90 is programmed to store the received flow signals and to compare each of the received flow signals with the alarm value established for the monitored flowline 16 associated with each such received flow signal. In the event any of the compared flow signals is smaller than the predetermined alarm value established for the monitored flowline 16 associated with that received flow signal for the predetermined alarm period of time established for the monitored flowline associated with that particular received flow signal, the processor 90 is programmed to provide an output no flow signal on the signal path 102.

The output signals on the signal path 102 from the processor 90 are received by the annunciator panel 100. The annunciator panel 100 is constructed and adapted to provide a visually perceivable output indication in response to a no flow signal received on the signal path 102 indicating that a problem production condition exists in the particular flowline associated with the flow signal which resulted in the no flow signal being produced by the processor 90. The annunciator panel 100 can include lamp indicators for providing the visually perceivable output indications in a manner like that described before with respect to the annunciator panel 80.

The processor 90 receives the flow signals from the other monitor stations 24, stores the received flow signals, compares each received flow signal with the stored alarm values for respective monitored flowlines 16 and provides the no flow signals for causing the annunciator panel 100 to provide the visually perceivable output indications in a manner exactly like that described before with respect to the monitor station 24a.

The processor 90 also is programmed to provide the stored flow signals on the signal path 98 to the permanent storage 96 in response to a received store data command manually inputted by way of the keyboard 104. The permanent storage 96 permanently stores the flow signals for each of the monitored flowlines 16 to provide historical data relating to the fluid flow through the various monitored flowlines 16.

The monitoring system of the present invention provides a means for periodically evaluating the performance of the various wells by comparing a recently determined production flow characteristics profile with a previously determined production flow characteristics profile for the particular flowline connected to the well of interest. Also, it has been found that it is a desirable practice when utilizing the present invention in connection with producing wells to re-establish the production flow characteristics profile for each of the monitored flowlines 16 from time-to-time during the operation of the present invention, and to redetermine the respective alarm values and alarm delay times from each such re-established production flow characteristics profile, since the flow characteristics may change from time-to-time for various reasons.

In a preferred operation, the system of the present invention also includes a testing or performance maintenance inspection mode of operation. In this mode of operation, the signal path connected to one of the transducers 22 is removed, such as removing one of the signal paths 36, 38, 40 and 42 from one of the transducers 22a, 22b, 22c and 22d, respectively. A test transducer which is constructed exactly like the transducers 22 is connected to the signal path 36, 38, 40 or 42 previously disconnected from one of the transducers 22. The test transducer has a known carrier and an audio signal having a known frequency, such as less than 1.0KHz, for example, is induced on the test transducer output carrier signal. The test transducer output signal is received by the monitor station 24 and transmitted to the base monitor station 26 where the received signal is plotted out by strip chart recorder 114, in a manner exactly like that described before with respect to the flow signals. Since the test transducer output signal is predetermined, one can determine if the various components of the present system are functioning in a proper manner from the plotted output printed by the strip chart recorder 114.

In one preferred embodiment, each monitor station 24 is assigned a unique identification code and the base monitor station 26, more particularly, is adapted to poll the various monitor stations 24 utilizing the identification codes. In this manner, the base monitor station 26 only is receiving signals from one of the monitor stations 24 at any given time. In this form, the base monitor station 24 sends a signal encoded with the identification code of one of the monitor stations 24 and, in response to receiving such a signal, the particular monitor station 24 identified by the encoded identification code transmits the information (flow signals) for reception at the base monitor station 26.

It should be noted that, although the present invention has been described with respect to monitoring production of off-shore wells or flowlines connected with such off-shore wells, the present invention can be used to monitor flow lines connected to wells on land. Further, the base monitor station 24 could be located on land in a system for monitoring production of off-shore wells in some applications.

Also, it should be noted that, although the monitoring system of the present invention has been described herein as including flow signals indicative of the velocity of the fluids passing through the monitored pipelines, other transducers may be used which provide flow signals indicative of some other fluid flow parameter.

Further, it should be noted that the present invention provides a means for monitoring fluid flow through flowlines and, in some applications, the flowlines might be associated with things other than wells. In other words, the present invention is not limited to monitoring production from wells.

Changes may be made in the construction and operation of the various elements, assemblies and components described herein and in the steps or the sequences of the steps of the method described herein without departing from the spirit and scope of the invention as defined in the following claims.

What is claimed is:

1. A monitoring system for monitoring fluid flow passing through a monitored flowline, comprising:

a transducer connected to the monitored flowline and adapted to detect the flow of fluids passing through the monitored flowline, the transducer being adapted to provide a flow signal proportional to the velocity of fluid flowing through the monitored flowline; and means for receiving the flow signals provided by the transducer, said means including a portion having a predetermined alarm value and a predetermined alarm delay time stored therein wherein the alarm value and the alarm delay time is predetermined for the monitored flowline, said alarm value being a velocity having a value between about fifty percent (b 50%) and about twenty percent (20%) of a predetermined maximum value of the velocity of the fluid flowing through the monitored flowline where the values of the velocity of the fluid flowing through the monitored flowline substantially vary over a predetermined period of time and said alarm value being a velocity having a value slightly less than a predetermined minimum value of the velocity of the fluid flowing through the monitored flowline where the values of the velocity of the fluid flowing through the monitored flowline are relatively constant over a predetermined period of time, and said alarm delay time being a period of time sufficient to encompass at least about three predetermined maximum velocity peaks of the fluid flowing through the monitored flowline and in excess of a predetermined minimum period of time, and said means providing an output indication in response to receiving a flow signal from the transducer indicating the velocity of the fluid flowing through the monitored flowline to have a value below the predetermined alarm value for a period of time in excess of the predetermined alarm delay time, thereby indicating a problem production condition in the fluid flow passing through the monitored flowline.

2. The monitoring system of claim 1 defined further as being for monitoring fluid flow passing through a plurality of monitored flowlines and defined further to include a plurality of transducers, each transducer being connected externally to one of the monitored flowlines, and each transducer being adapted to detect the flow of fluids passing through the monitored flowline connected thereto and each transducer being adapted to provide a flow signal proportional to the velocity of the fluid flowing through the monitored flowline connected thereto; and wherein the means for receiving the flow signals is defined further as receiving each of the flow signals provided by the transducers, said means including a portion having a plurality of alarm values and a plurality of predetermined alarm delay times stored therein wherein each alarm value and each alarm delay time is predetermined for one of the monitored flowlines, and said means providing an output indication in response to receiving a flow signal from any one of the transducers indicating a velocity of the fluid flowing through the monitored flowline connected to such transducer having a value below the predetermined alarm value (determined for the monitored flowline connected to the transducer producing such received flow signal) for a period of time in excess of the predetermined alarm delay time (determined for the monitored flowline connected to the transducer producing such received flow signal), thereby indicating a problem production condition in the fluid flow passing through that monitored flowline.

3. The monitoring system of claim 2 wherein the means for receiving the flow signals is defined further to include:

a time-share network adapted to receive each flow signal and sequentially to provide the received flow signals on an output signal path;

a processor adapted to receive the flow signals provided by the time-share network, the predetermined alarm value and the predetermined alarm delay time for each monitored flowline being stored in the processor, the processor being adapted to compare each of the received flow signals provided the transducers with the predetermined alarm value and the predetermined alarm delay time established for the monitored flowline connected to the transducer producing such received flow signal and to provide an output no flow signal indicating a problem production condition in response to receiving a flow signal from any one of the transducers indicating a velocity of the fluid below the alarm value (determined for the monitored flowline connected to the transducer producing such received flow signal) for a period of time in excess of alarm delay time (determined for the monitored flowline connected to the transducer producing such received flow signal; and an annunciator panel receiving the no flow signal from the processor and providing an output indication indicating a problem production condition for the particular monitored flowline connected to the transducer producing the flow signal which resulted in the no flow signal.

4. The monitoring system of claim 3 wherein the processor is defined further as being adapted to receive the flow signals and store the flow signals received from each transducer and the time each such received flow signal was received for a predetermined period of time sufficient to establish a production flow characteristics profile for each monitored flowline, and wherein the processor is defined further as being adapted to receive a print command signal, and wherein the processor is defined further as providing on an output signal path the received flow signals and associated time for each such flow signal for each respective monitored flowline in response to receiving the print command signal, and wherein the monitoring system is defined further to include:

a strip chart recorder connected to the processor and being adapted to receive from the processor the flow signals and the associated time for each such flow signal, and to provide an output in a printed form plotting the flow signals with respect to time (production flow characteristics profile for the monitored flowline having the transducer connected thereto associated with such received flow signals), the alarm values and the alarm delay times being determined from the respective production flow characteristics profiles for the monitored flowlines.

5. The monitoring system of claim 4 defined further to include:
a digital to analog converter generally between the processor and the strip chart recorder, the digital to analog recorder receiving the flow signals in a digital form from the processor and providing the received flow signals in an analog form on an output signal path for reception by the strip chart recorder, the strip chart recorder receiving the flow signals in an analog form from the digital to analog converter and providing the production flow characteristics profiles.

6. The monitoring system of claim 3 wherein each of the transducers is defined further as being adapted to receive a transducer operating signal having a frequency in the ultrasonic frequency range and to an output signal (flow signal) having a carrier in the ultrasonic frequency modulated in proportion to the velocity of the fluid flowing through the monitored flowline connected thereto, and wherein the monitoring system is defined further to include:
an amplifier detector receiving the flow signals from the time-share network and amplifying and detecting the received flow signals, the amplifier detector providing the amplified and detected flow signals on an output signal path;
a frequency to voltage converter receiving the amplified and detected flow signals and providing a DC analog voltage output signal (flow signal) proportional to the velocity represented by the received flow signal; and
an analog to digital converter receiving the flow signals from the frequency to voltage converter and providing the received flow signals in a digital form on an output signal path, the flow signals in a digital form being received by the processor.

7. The monitoring system of claim 6 defined further to include:
a signal generator providing transducer operating signals having a frequency in the ultrasonic frequency range for reception by the Doppler shift transducer.

8. The monitoring system of claim 7 defined further to include:
a power booster receiving the transducer operating signals from the signal generator and increasing the power level of the transducer operating signals, the power booster being a unity gain buffer amplifier and the transducer operating signals from the power booster being received by the transducers permitting a relatively longer signal path to be utilized in connecting such transducer operating signals to the Doppler shift transducer.

9. The monitoring system of claim 2 wherein each of the monitored flowlines is connected to a well, the fluid flow from each well passing through one of the monitored flowlines.

10. The monitoring system of claim 9 wherein the wells are off-shore wells and wherein a portion of each of the monitored flowlines is disposed underwater.

11. The monitoring system of claim 1 wherein the transducer is further defined as being a Doppler shift transducer externally connected to the monitored flowline.

12. A monitoring system for monitoring fluid flow passing through a plurality of monitored flowlines, comprising:
a plurality of transducers, each transducer being connected to one of the monitored flowlines, and each transducer being adapted to detect the flow of fluids passing through the monitored flowline connected thereto and each transducer being adapted to provide a flow signal proportional to the velocity of the fluid flowing through the monitored flowline connected thereto;
at least two monitor stations, each monitor station comprising:
a time-share network adapted to receive the flow signals provided by the tranducers connected to some of the monitored flowlines and sequentially to provide the received flow signals on an output signal path;
a processor adapted to receive the flow signals provided by the time-share network, the processor providing the flow signals on an output signal path; and
a transmitter-receiver receiving the flow signals provided by the processor and transmitting the received flow signals; and
a base monitor station, comprising:
a transmitter-receiver receiving the flow signals transmitted by the transmitter-receiver in each of the monitor stations and providing the received flow signals on an output signal path;
a processor adapted to receive the flow signals provided by the transmitter-receiver, a predetermined alarm value and a predetermined alarm delay time for each monitored flowline being stored in the processor, the processor being adapted to compare each of the received flow signals provided the transducers with the predetermined alarm value and the predetermined alarm delay time established for the monitored flowline connected to the transducer producing such received flow signal and to provide an output no flow signal indicating a problem production condition in response to receiving a flow signal from any one of the transducers indicating a velocity of the fluid below the alarm value (determined for the monitored flowline connected to the transducer producing such received flow signal) for a period of time in excess of alarm delay time (determined for the monitored flowline connected to the transducer producing such received flow signal); and
an annunciator panel receiving the no flow signal from the processor and providing an output indication indicating a problem production condition for the particular monitored flowline connected to the transducer device producing the flow signal which resulted in the no flow signal.

13. The monitoring system of claim 12 wherein the processor in each of the monitor stations is defined further as having the predetermined alarm value and the predetermined alarm delay time for each monitored flowline having the transducers connected thereto producing the flow signals received by the time-share network being stored in the processor, the processor being adapted to compare each of the received flow signals provided the transducers with the predetermined alarm value and the predetermined alarm delay time established for the monitored flowline connected to the transducer producing such received flow signal and to provide an output no flow signal indicating a problem production condition in response to receiving a flow signal from any one of the transducers indicating a velocity of the fluid below the alarm value (determined for the monitored flowline connected to the transducer producing such received flow signal) for a period of time in excess of alarm delay time (determined for the monitored flowline connected to the transducer producing such received flow signal), and wherein each monitor station is defined further to include:

an annunciator panel receiving the no flow signal from the processor in the monitor station and providing an output indication indicating a problem production condition for the particular monitored flowline connected to the transducer device producing the flow signal which resulted in the no flow signal.

14. The monitoring system of claim 13 wherein the alarm value is defined further as being a velocity having a value between about fifty percent (50%) and about twenty percent (20%) of a predetermined maximum value of the velocity of the fluid flowing through the monitored flowline where the values of the velocity of the fluid flowing through the monitored flowline substantially vary over a period of time and a velocity having a value slightly less than a predetermined minimum value of the velocity of the fluid flowing through the monitored flowline where the values of the velocity of fluid flowing through the monitored flowline are relatively constant over a period of time.

15. The monitoring system of claim 14 wherein the alarm delay time is defined further as being a period of time sufficient to encompass at least about three predetermined maximum velocity peaks of the fluid flowing through the monitored flowline and in excess of a predetermined maximum period of time.

16. The monitoring system of claim 12 wherein the processor in the base monitor station is defined further as being adapated to receive the flow signals and store the flow signals received from each transducer and the time of each such received flow signal for a predetermined period of time sufficient to establish a production flow characteristics profile for each monitored flowline, and wherein the processor in the base monitor station is defined further as being adapted to receive a print command signal, and wherein the processor in the base monitor station is defined further as providing on an output signal path the received flow signals and associated time of each such flow signal for each respective monitored flowline in response to receiving the print command signal, and wherein the base monitor station is defined further to include:

a strip chart recorder connected to the processor in the base monitor station and being adapted to receive from the processor in the base monitor station the flow signals and the associated times of each such flow signal, and to provide an output in a printed form plotting the flow signals with respect to time (production flow characteristics profile for the monitored flowline having the transducer connected thereto associated with such received flow signals), the alarm values and the alarm delay times being determined from the respective production flow characteristics profile for the monitored flowlines.

17. The monitoring system of claim 16 defined further to include:

a digital to analog converter generally between the processor in the base monitor station and the strip chart recorder, the digital to analog recorder receiving the flow signals in a digital form from the processor in the base monitor station and providing the received flow signals in an analog form on an output signal path for reception by the strip chart recorder, the strip chart recorder receiving the flow signals in an analog form from the digital to analog converter and providing the production flow characteristics profiles.

18. The monitoring system of claim 12 wherein each of the transducers is defined further as being adapted to receive a transducer operating signal having a frequency in the ultrasonic frequency range and to an output signal (flow signal) having a carrier in the ultrasonic frequency modulated in proportion to the velocity of the fluid flowing through the monitored flowline connected thereto, and wherein each monitor station is defined further to include:

an amplifier detector receiving the flow signals from the time-share network and amplifying and detecting the received flow signals, the amplifier detector providing the amplified and detected flow signals on an output signal path;

a frequency to voltage converter receiving the amplified and detected flow signals and providing a DC analog voltage output signal (flow signal) proportional to the velocity represented by the received flow signal; and     an analog to digital converter receiving the flow signals from the frequency to voltage converter and providing the received flow signals in a digital form on an output signal path, the flow signals in a digital form being received by the processor in the monitor station.

19. The monitoring system of claim 18 wherein each monitor station is defined further to include:

a signal generator providing transducer operating signals having a frequency in the ultrasonic frequency range.

20. The monitoring system of claim 12 wherein the transducer is further defined as being a Doppler shift transducer externally connected to the monitored flowline.

21. A method for monitoring fluid flow passing through a monitored flowline comprising the steps of:

producing flow signals proportional to the velocity of the fluid flowing through the monitored flowline;

receiving the fluid flow signals over a predetermined period of time and establishing the time each such flow signal was received; and     processing the received flow signals proportional to the velocity of the fluid flow with respect to time for the monitored flowline for the predetermined period of time sufficient to establish a repeatable pattern in the velocity of the fluid flowing through the monitored flowline versus time, to provide production flow characteristics profile for the monitored flowline and utilizing the same to indicate a problem production in the fluid flow passing through the monitored flowline.

22. The method of claim 21 defined further as being for monitoring the fluid flow passing through a plurality of monitored flowlines, and wherein the step of producing flow signals is defined further as producing flow signals proportional to the velocity of the fluid flowing through each respective monitored flowline, and wherein the step of receiving the flow signals is defined further as receiving the flow signals proportional to the velocity of the fluid flowing through each respective monitored flowline over a predetermined period of time and determining the time each such flow signal was received, and wherein the step of processing the flow signals is defined further as processing the received flow signals proportional to the velocity of the fluid flowing through each respective monitored flowline with respect to time for each monitored flowline, to provide a production flow characteristics profile for each monitored flowline and utilizing the same to indicate a problem production condition in the fluid flow passing through the monitored flowline.

23. The method of claim 22 wherein the steps of processing the flow signals to provide the production flow characteristics profile and utilizing the same to indicate problem production conditions is defined further to include the step of:
  determining for each monitored flowline from the respective production flow characteristics profile an alarm value;
  determining for each monitored flowline from the respective production flow characteristics profiles an alarm delay time;
  receiving the fluid flow signals after determining the alarm values and the alarm delay times;
  comparing the velocity indicated by each received flow signal with the alarm value determined for the monitored flowline associated with such received flow signal; and
  providing a no flow signal in response to a comparison indicating the velocity of the fluid flowing through the monitored flowline is below the alarm value for a period of time in excess of the alarm delay time.

24. The method of claim 23 wherein each alarm value is defined further as being a value between about fifty percent (50%) and about twenty percent (20%) of a predetermined maximum value of the velocity of the fluid flowing through the monitored flowline where the values of the velocity of the fluid flowing through the monitored flowline substantially vary over a period of time and a velocity having a value slightly less than a predetermined minimum value of the velocity of the fluid flowing through the monitored flowline where the values of the velocity of fluid flowing through the monitored flowline are relatively constant over a period of time; and wherein each alarm delay time is defined further as being a period of time sufficient to encompass at least about three predetermined maximum velocity peaks of the fluid flowing through the monitored flowline and in excess of a predetermined maximum period of time.

25. The method of claim 23 defined further to include the step of:
  receiving the no flow signals and providing a visually perceivable output indication in response to receiving each no flow signal for indicating a problem production condition in one of the monitored flowlines.

26. The method of claim 23 wherein the step of producing the flow signals is defined further to include the steps of:
  connecting a Doppler shift transducer externally to each of the monitored flowlines, each transducer being capable of receiving a transducer operating signal;
  producing the transducer operating signals;
  receiving at each transducer the transducer operating signals; and
  providing at each transducer the flow signals proportional to the velocity of the fluid flowing through the monitored flowline having such transducer connected thereto.

27. The method of claim 26 wherein the step of producing the transducer operating signals is defined further as providing the transducer operating signals having a frequency in the ultrasonic frequency range, and wherein the step of providing the flow signals is defined further as providing the flow signals at each transducer, each transducer producing flow signals having a carrier in the ultrasonic frequency range modulated in proportion to the velocity of the fluid flowing through the monitored flowline connected thereto, and wherein the step of receiving the flow signals is defined further to include the steps of:
  receiving sequentially the flow signals from each of the transducers;
  amplifying and detecting each of the received flow signals;
  converting the detected flow signals from an analog form of flow signal to a digital form of flow signal; and
  receiving the flow signals in the digital form and storing the received flow signals over the predetermined period of time, along with the time each such flow signal was received from the respective transducers; and
wherein the step of receiving the flow signals after determining the alarm values and the alarm delay times as defined further to include the steps of:
  receiving sequentially the flow signals from each of the transducers;
  amplifying and detecting each of the received flow signals;
  converting the detected flow signals from an analog form of flow signal to a digital form of flow signal; and
  receiving the flow signals in the digital form.

28. The method of claim 21 wherein each of the monitored flowlines is connected to a well, the fluid flow from each well flowing through one of the monitored flowlines.

29. The method of claim 28 wherein the wells are offshore wells and wherein a portion of each of the monitored flowlines is disposed underwater.

30. A monitoring system for monitoring fluid flow passing through a monitored flowline, comprising:
  a transducer connected to the monitored flowline, and being adapted to detect the flow of fluids passing through the monitored flowline, the transducer being adapted to provide a flow signal proportional to the velocity of the flow of fluid through the monitored flowline; and
  means for receiving the flow signals provided by the transducer, said means being adapted to store the flow signals received from the transducer and the time each such flow signal was received for a predetermined period of time sufficient to establish a repeatable pattern in the velocity of the fluid flowing through the monitored flowline versus time to establish the production flow characteristic profile for the monitored flowline, said means being adapted to provide on an output signal path the received flow signals and associated time of each such flow signal and means for utilizing the same to provide an output indication indicating a problem production condition for the monitored flowline.

31. The monitoring system of claim 30 defined further as being for monitoring fluid flow passing through a plurality of monitored flowlines, and wherein the monitoring system is defined further to include a plurality of transducers, each transducer being connected to one of the monitored flowlines, each transducer being adapted to detect the flow of fluids passing through the monitored flowline connected thereto, and each transducer being adapted to provide a flow signal proportional to a fluid flow parameter indicative of the flow of fluid through the monitored flowline connected thereto; and wherein the means for receiving the flow signals is defined further as receiving the flow signals provided by each of the transducers, said means being adapted to store the flow signals received from each of the transducers and the time each such flow signal was received for a predetermined period of time sufficient to establish the production flow characteristics profile for each of the monitored flowlines, said means being adapted to provide on an output signal path the received flow signals and associated time of each such flow signal for each respective monitored flowline; and wherein the means for receiving the flow signals is defined further as receiving the flow signals and the associated time of each such flow signal associated with each transducer, and providing an output in a printed form plotting for each of the monitored flowlines the respective flow signals with respect to time (the production flow characteristics profile).

32. The monitoring system of claim 31 wherein the means for utilizing the same to provide an output indication indicating a problem production condition is defined further to include: means for receiving the flow signals including a portion having a predetermined alarm value and a predetermined alarm delay time stored therein wherein the alarm value and the alarm delay time are determined for the monitored flowline from the production flow characteristics for the particular monitored flowline, and said means providing an output indication in response to receiving a flow signal from the transducer indicating a fluid flow velocity in the monitored flowline having a value below the predetermined alarm value for a predetermined period of time in excess of the predetermined alarm delay, thereby indicating a problem production condition in the fluid flow passing through the monitored flowline, wherein the alarm value is defined further as being a velocity having a value between about fifty percent (50%) and about twenty percent (20%) of a predetermined maximum value of the velocity of the fluid flowing through the monitored flowline where the values of the velocity of the fluid flowing through the monitored flowline substantially vary over a period of time and a velocity having a value slightly less than a predetermined minimum vlaue of the velocity of the fluid flowing through the monitored flowline where the values of the velocity of fluid flowing through the monitored flowline are relatively constant over a period of time.

33. The monitoring system of claim 32 wherein the alarm delay time is defined further as being a period of time sufficient to encompass at least about three predetermined maximum velocity peaks of the fluid flowing through the monitored flowline and in excess of a predetermined maximum period of time.

34. The monitoring system of claim 31 wherein the means for receiving the flow signals is defined further to include;
 a time-share network adapted to receive each flow signal and sequentially to provide the received flow signals on an output signal path;
 a processor adapted to receive the flow signals provided by the time-share network and received from each transducer and the time each such flow signal was received for a predetermined period of time sufficient to establish the production flow characteristics profile for each monitored flowline, the processor being adapted to receive a print command signal, and the processor providing on an output signal path the received flow signals and associated time for each such flow signal for each respective monitored flowline in response to receiving the print command signal; and
wherein the means for plotting each production flow characteristics profile is defined further to includes:
 a strip chart recorder connected to the processor and being adapted to receive from the processor the flow signals and the associated relative times for each such flow signal, and to provide an output in a printed form plotting the flow signals with respect to time (production flow characteristics profile for the monitored flowline having the transducer connected thereto associated with such received flow signals).

35. The monitoring system of claim 34 wherein the means for plotting the production flow characteristics profiles is defined further to include:
 a digital to analog converter generally between the processor and the strip chart recorder, the digital to analog recorder receiving the flow signals in a digital form from the processor and providing the received flow signals in an analog form on an output signal path for reception by the strip chart recorder, the strip chart recorder receiving the flow signals in an analog form from the digital to analog converter and providing the production flow characteristics profiles.

* * * * *